(12) United States Patent
Pajkovic et al.

(10) Patent No.: US 11,992,694 B2
(45) Date of Patent: May 28, 2024

(54) BUILDING BLOCK FOR ELECTRO-OPTICAL INTEGRATED INDIUM-PHOSPHIDE BASED PHASE MODULATOR

(71) Applicant: SMART PHOTONICS HOLDING B.V., Eindhoven (NL)

(72) Inventors: Rastko Pajkovic, Eindhoven (NL); Erwin Antonius Josephus Maria Bente, Eindhoven (NL); Stefanos Andreou, Eindhoven (NL); Theodorus Thomas Marinus Van Schaijk, Eindhoven (NL)

(73) Assignee: SMART PHOTONICS HOLDING B.V., Eindhoven (NL)

( * ) Notice: Subject to any disclaimer, the term of this patent is extended or adjusted under 35 U.S.C. 154(b) by 254 days.

(21) Appl. No.: 17/395,771

(22) Filed: Aug. 6, 2021

(65) Prior Publication Data

US 2021/0376557 A1   Dec. 2, 2021

Related U.S. Application Data

(63) Continuation of application No. PCT/NL2020/050069, filed on Feb. 7, 2020.
(Continued)

(51) Int. Cl.
*A61N 2/00* (2006.01)
*A61K 45/06* (2006.01)
(Continued)

(52) U.S. Cl.
CPC ............. *A61N 2/004* (2013.01); *A61K 45/06* (2013.01); *A61N 2/002* (2013.01); *A61N 2/02* (2013.01);
(Continued)

(58) Field of Classification Search
None
See application file for complete search history.

(56) References Cited

U.S. PATENT DOCUMENTS 3,993,963 A * 11/1976 Logan .................. C30B 19/063
148/33.5
5,978,402 A * 11/1999 Matsumoto ........... H01S 5/0265
372/50.1
(Continued)

FOREIGN PATENT DOCUMENTS

JP      H06204549 A    7/1994
JP      H10173291 A    6/1998
(Continued)

OTHER PUBLICATIONS

International Search Report and Written Opinion dated Apr. 28, 2020 for PCT Application No. PCT/NL2020/050069.
(Continued)

*Primary Examiner* — Jerry Rahll
(74) *Attorney, Agent, or Firm* — EIP US LLP

(57) ABSTRACT

A photonic integrated circuit, PIC, comprising a plurality of semiconductor layers on a substrate, the plurality of semiconductor layers forming a PIN or PN doping structure, the PIC comprising a waveguide arranged for conducting light waves; an optical element connected to the waveguide, wherein the optical element, in operation, is in reverse-bias mode, and wherein the optical element comprises a contact layer arranged for connecting to a voltage source; wherein the waveguide comprises conducting contacts proximal to the optical element, and wherein the PIC further comprises
(Continued)

at least one isolation section arranged in between the optical element and the conducting contacts. Corresponding methods of operation of such a PIC are also presented herein.

19 Claims, 3 Drawing Sheets

Related U.S. Application Data

(60) Provisional application No. 62/802,689, filed on Feb. 7, 2019.

(51) Int. Cl.
*A61N 2/02* (2006.01)
*G02B 6/122* (2006.01)
*G02F 1/025* (2006.01)
*H01S 5/026* (2006.01)
*A61B 5/055* (2006.01)
*A61B 6/00* (2006.01)
*A61B 6/03* (2006.01)
*A61B 6/50* (2024.01)

(52) U.S. Cl.
CPC ............ *G02B 6/122* (2013.01); *G02F 1/025* (2013.01); *H01S 5/026* (2013.01); *A61B 5/055* (2013.01); *A61B 6/032* (2013.01); *A61B 6/037* (2013.01); *A61B 6/50* (2013.01)

(56) References Cited

U.S. PATENT DOCUMENTS

| | | | | |
|---|---|---|---|---|
| 6,614,213 B1* | 9/2003 | Whitbread | ............ | G02F 1/2257 324/72 |
| 2002/0054724 A1* | 5/2002 | Tada | ............ | G02F 1/025 385/2 |
| 2011/0002352 A1* | 1/2011 | Takiguchi | ............ | H01S 5/026 372/50.1 |
| 2019/0317341 A1* | 10/2019 | Nishikawa | ............ | G02F 1/017 |

FOREIGN PATENT DOCUMENTS

| | | |
|---|---|---|
| JP | 2005223043 A | 8/2005 |
| JP | 2008065104 A | 3/2008 |
| JP | 2009163186 A | 7/2009 |
| JP | 2016029469 A | 3/2016 |
| WO | 2009087927 A1 | 7/2009 |
| WO | 2018131227 A1 | 7/2018 |

OTHER PUBLICATIONS

Augustin et al. "InP-Based Generic Foundry Platform for Photonic Integrated Circuits", IEEE Journal of Selected Topics in Quantum Electronics, vol. 24, No. 1, Jan. 1, 2018 (Jan. 1, 2018), pp. 1-10, XP011656818.

Yao et al., "Performance Degradation of Integrated Optical Modulators Due to Electrical Crosstalk", Journal of Lightwave Technology, IEEE, vol. 34, No. 13, Jul. 1, 2016 (Jul. 1, 2016), pp. 3080-3086, XP011615691.

Japanese Office Action dated Dec. 5, 2023 for Japanese Application No. 2021-539136.

* cited by examiner

BUILDING BLOCK FOR ELECTRO-OPTICAL INTEGRATED INDIUM-PHOSPHIDE BASED PHASE MODULATOR

CROSS-REFERENCE TO RELATED APPLICATIONS

This application is a continuation of International Application No. PCT/NL2020/050069, filed Feb. 7, 2020 which claims priority to U.S. Provisional Application No. 62/802,689, filed Feb. 7, 2019, under 35 U.S.C. § 119(a). Each of the above-referenced patent applications is incorporated by reference in its entirety.

BACKGROUND

Field of the Invention

The present disclosure generally relates to the field of photonic integrated circuits and in particular to a device with reduced interference levels between different components of the photonic integrated circuit.

Description of the Related Technology

A Photonic Integrated Circuit, PIC, or an integrated optical circuit is a device that integrates a plurality of photonic functions. It is mainly differentiated from an electronic integrated circuit by the fact that a PIC provides functions for information signals imposed on optical wavelengths in the visible or the near infrared spectrum. Different components such as low loss interconnect waveguides, power splitters, optical amplifiers, optical modulators, filters, lasers and detectors form a PIC. In general, a PIC comprises both active as well as passive components. Active components are, for example, Semiconductor Optical Amplifiers, SOA, Electro Refractive Modulators, ERMs and passive components are, for example, a waveguide.

Examples of PICs include monolithic tunable lasers, widely tunable lasers, externally modulated lasers and transmitters, integrated receivers. In such PICs the parameters of light such as frequency and phase are important and information may be communicated on the basis of a change in one of these properties. It is therefore desirable to be able to finely control such parameters.

For example, the phase of light is adjusted by employing an ERM. The ERM varies the phase by adjusting the refractive index of a material, which in turn can be controlled by influencing the Electrical field that is applied in the material. In normal practice, the electric field is accurately controlled by adjusting a biasing voltage.

Upon testing, it appears that there is a cross talk between active components thereby introducing additional electric fields which, in turn, influence the phase of the light passing through the active component. This is undesirable. Furthermore, such an additional electric field was also observed across the passive elements such as a waveguide as well. As a result the phase of the light passing through, changed beyond what was expected.

The present inventors have identified a problem with the standard phase modulators, which are ERMs, in the generic multi-project wafer, MPW, integration process when used in reverse bias. This problem motivated a discovery that also addresses similar issues with other components in Indium Phosphide, InP, MPW process, and not just phase modulators.

The problem was found during the characterization of a tunable laser with the filter based on the three Asymmetric Mach-Zehnder interferometers, AMZI, in series. This particular device was realized in a MPW run of Smart Photonics run 17, SP17, on an n-doped substrate and packaged in a Technobis standard package. The lay-out of the device is schematically depicted in FIG. 1, and is elaborated further with reference to FIG. 1

This device 1 has three AMZIs, 10, 20, 30 each with two ERMs 11, 12; 21, 22; 31, 32; that are 2.118 mm long plus a so-called in-line ERM 40 to tune the cavity mode independently. All ERMs have isolation sections at both ends that are 30 micro meter, µm, long. The ERMs are operated using a voltage that put the pin-junction in the device under reverse bias.

We have found that in this circuit there are two related issues. The first issue is that there can be a significant amount of electrical cross-talk between the different ERMs. The second issue, which is directly related, is that passive waveguides between two ERMs are biased as a consequence of the biasing of the surrounding ERMs and act as phase modulators. The issues become visible in the results from measurements on the laser, which are presented here. In this measurement the long waveguide arm of the coarse tuning (smallest path length difference) AMZI is reversely biased with a voltage Vset. The voltage levels at the other, unbiased ERMs were measured using a Keithley source-meter. The chip was grounded at the bottom n-contact. The measurement results are presented in FIG. 2. Presented are the voltages recorded on the ERM in 51 the short arm of the coarse tuning AMZI; 52 the long arm of the middle AMZI; 53 the long arm of the fine tuning AMZI as a function of the voltage Vset.

The cross-talk to the different ERMs is clearly visible. This implies that the passive waveguides and MMIs between the ERMs have a voltage on the p-doped layer. Therefore they will also act as a phase modulator. More data on the tuning of the AMZIs are available that also highlight the effect of the passive waveguides.

The origin of the cross-talk is the fact that the isolation sections have a resistance of a few mega ohms, MΩ, and the resistance of the reverse biased pin diode structure is similar or higher. The reverse bias current (in the dark) at −4 Volts, V, is 80 to 100 Nano-Amperes, nA, which means a resistance of the order of 40 MΩPlease note that when light travels through the ERM it influences the current through the ERM and thus its effective resistance. This will affect crosstalk to the passive waveguide sections and other ERMs.

SUMMARY

In a first aspect of the present disclosure, there is presented a photonic integrated circuit, PIC, comprising a plurality of semiconductor layers on a substrate, the plurality of semiconductor layers forming a PIN or PN doping structure, the PIC comprising a waveguide comprising a waveguiding layer, which is one of the layers of the plurality of semiconductor layers, and arranged for conducting light waves, an optical element comprising a waveguiding layer, which is one of the layers of the plurality of semiconductor layers, which waveguiding layers of the waveguide and the optical element are connected to one another, wherein the optical element, in operation, is in reverse-bias mode, and wherein the optical element comprises a contact layer arranged for connecting to a voltage source; wherein the waveguide comprises at least one conducting contact proximal to the optical element, and wherein the PIC further comprises at least one isolation section arranged in between the contact layer and the at least one conducting contact.

As understood in the art, A Photonic Integrated Circuit, PIC, or an integrated optical circuit is a device that integrates a plurality of photonic functions. A PIC may in turn comprise of several active and/or passive components. The PIC is usually formed by arranging several layers of semiconductor material upon a substrate. The layers are doped so as to form a PIN or PN doping structure. An example of such a doping structure is presented in FIG. 3b and is described in detail in the corresponding section below.

As identified, in the previous section, the inventors found that in spite of the isolation section, comprised in elements of a PIC, there are undesirable effects such as occurrence of cross talk between the components or passive components such as waveguides introducing additional phase modulation. It was the inventors' insight that by providing an additional at least one conducting contact proximal to the contact layer such that the optical elements can be effectively isolated from the effects of a neighbouring optical element.

According to an embodiment, the at least one isolation section is arranged in between the optical element and the conducting contacts.

For example the isolation section may assure that multiple layers of the semiconductor layers of the optical element and the waveguide are isolated, such that not all semiconductor layers of the optical element also directly connect with their respective counterpart semiconductor layer of the waveguide.

According to an embodiment, the at least one conducting contact is configured on both sides of the optical element, with respect to a direction of light in the waveguide. This is a preferred configuration that ensures improved isolation of the optical element in question.

According to an embodiment, the at least one conducting contact extends over substantially the entire waveguide. The inventors consider it advantageous to ensure effective isolation of the waveguide by placing the at least one conducting contact over substantially the entire waveguide. In this manner, the waveguide remains passive and is not biased due to the neighbouring electric fields.

In an exemplary embodiment, the at least one conducting contact is connected to an electrical ground. This has an advantage that the isolation becomes more effective. The electrical grounding may be achieved, with the help of a grounding hole arranged for allowing a contact between a conducting contact and an n-doped layer wherein distance between an edge of the grounding hole and the waveguide is at least 10 µm, wherein the distance is measured in a direction perpendicular to that of propagation of light in the waveguide. In a preferred embodiment it may be advantageous to maintain a specific voltage on the metal contact.

As mentioned, the length is measured in direction perpendicular to the direction of propagation of light. The value of 10 µm is chosen such that any bias applied to the conducting contacts does not affect the propagation of light in the waveguide. Current technological restrictions dictate that such a distance be at least 10 µm at present. The skilled person understands that this distance may be further reduced in the future if technological improvement allow for such a reduction in the distance. The determining factor is that the distance should be chosen such that the bias applied to the conducting contact does not affect propagation of light in a way that is detrimental to the functioning of the device.

Preferably, at least one dimension of a cross section of the grounding hole in a plane parallel to the direction of propagation of light in the waveguide is at least 20 µm. Such a limitation is also a result of the current technology used. Future technologies may allow for smaller sizes of grounding holes.

According to an embodiment, the length of the conducting contacts measured in the direction of propagation of light is at least 20 µm. The inventors considered that in order to achieve isolation in a more efficient manner, it is desirable to ensure that the conducting contacts extend for at least 20 µm, and more preferably for at least 50 µm.

According to any one of the embodiments, the conducting contact comprise any of Titanium and/or Gold and/or Platinum. The inventors recognized that these are the metals that are commonly employed during the fabrication of such PICs. The skilled person is also aware of other metal or materials of suitable conductivity that may be employed by in order to achieve the objectives as listed out in the present disclosure.

According to the present disclosure, the optical element is any of a

Electro-Refractive Modulator, ERM, and

Photodetector.

The inventors considered these two elements to be most susceptible to surrounding electric fields and consider it advantageous to ensure isolation for these two elements. For example, the ERM modulates the phase of the light by adjusting the refractive index of the material. The refractive index, is in turn adjusted by varying the electric field. Therefore, if the ERM is not effectively isolated, an undesired or unexpected phase output is observed.

According to an embodiment, the PIC comprises a plurality of conducting contacts, wherein the plurality of conducting contacts are connected to one another by means of a metallic conducting layer. In such an embodiment all the conducting proximal to different optical elements are all connected to one another. This can be advantageous in that only one electrical ground may be required.

In a second aspect of the present invention, there is presented a method of operating a photonic integrated device according to the present disclosure, as discussed above, wherein a reverse bias voltage is applied to the conducting contacts. The inventors consider it advantageous to connect the conducting contacts to voltage source and to apply a reverse bias voltage thereto. This has the effect that it reduces propagation losses and stabilizes the optical path length to a higher degree than the current situation. This is particularly useful when applied the reverse bias is applied to conducting contacts over passive components such as a waveguide.

In another embodiment of the second aspect of the present disclosure, there is presented a method of operating a photonic integrated device according to the present disclosure, as discussed above, wherein the conducting contacts are connected to an electrical ground. Instead of connecting, the contacts to a reverse bias, the conducting contacts may also be grounded. The invention is understood in more detail with reference to the figures and the description thereof.

DETAILED DESCRIPTION

Figure 1:
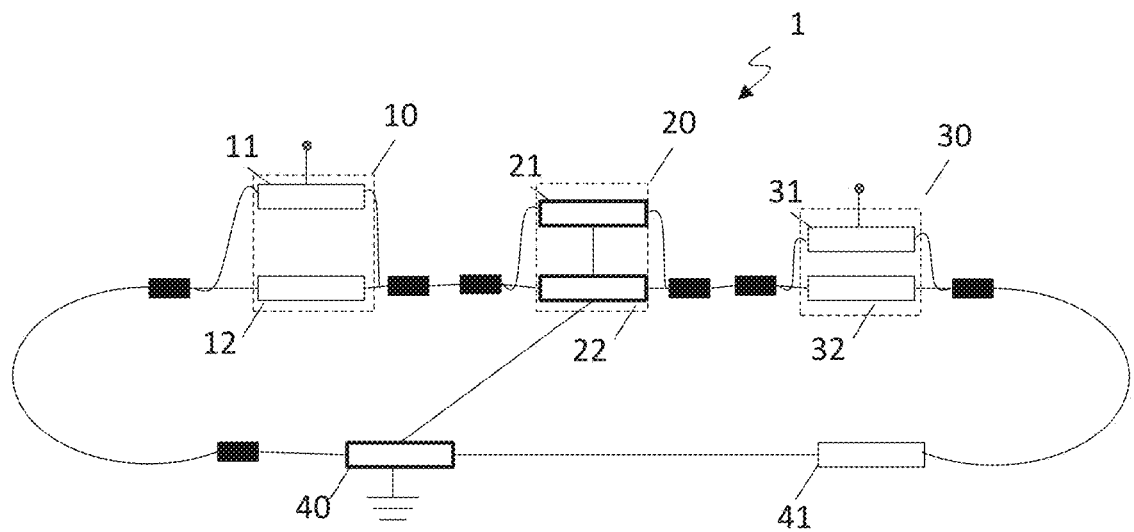
FIG. 1 illustrates a schematic layout of a tunable laser as commonly employed in a Photonic Integrated Circuit, PIC.

FIG. 1 illustrates a schematic layout of a tunable laser as commonly employed in a Photonic Integrated Circuit, PIC. This device 1 has three AMZIs, 10, 20, 30 each with two ERMs 11, 12; 21, 22; 31, 32; that are 2.118 mm long plus a so-called in-line ERM 40 to tune the cavity mode independently. All ERMs have isolation sections at both ends that are 30 µm long. The ERMs are operated using a voltage that put the pin-junction in the device under reverse bias. The layout also comprises a semiconductor optical amplifier, SOA, 41.

Figure 2:
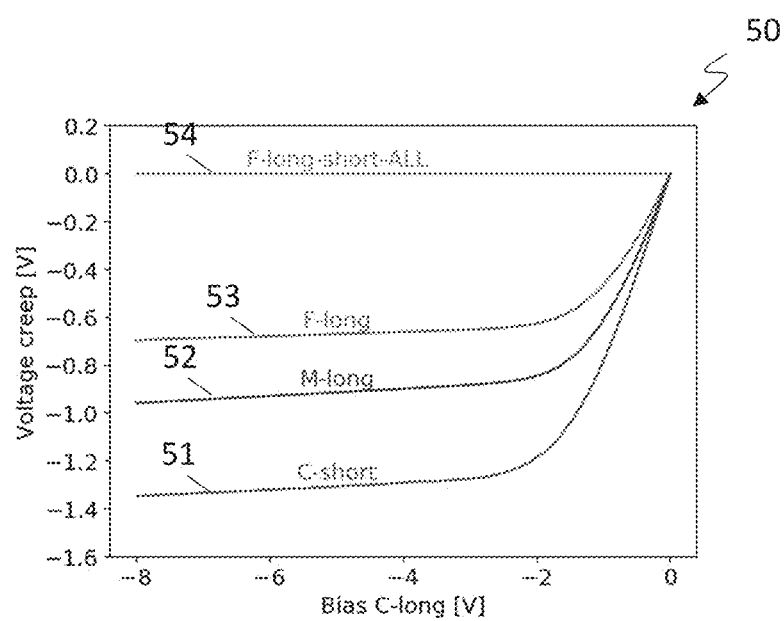
FIG. 2 illustrates voltage levels measured on the different Electro-Refractive modulators, ERMs, as a function of the voltage applied to the ERM in the long arm of the coarse tuning AMZI.

FIG. 2 illustrates, in 50, voltage levels measured on the different Electro-Refractive modulators, ERMs, as a function of the voltage applied to the ERM in the long arm of the coarse tuning AMZI. Presented are the voltages recorded on the ERM in 51 the short arm of the coarse tuning AMZI; in 52, the long arm of the middle AMZI; and in 53, the long arm of the fine tuning AMZI In 54 the measured voltage on the fine tuning AMZI is presented when the cavity ERM and the two ERMs in the medium tuning AMZI are grounded. This clearly points that by effectively grounding the optical elements, the interference in other neighbouring optical elements can be effectively reduced. The latter observation points towards a possible solution and improvement of the ERM building block. This is depicted in FIG. 3.

Figure 3A:
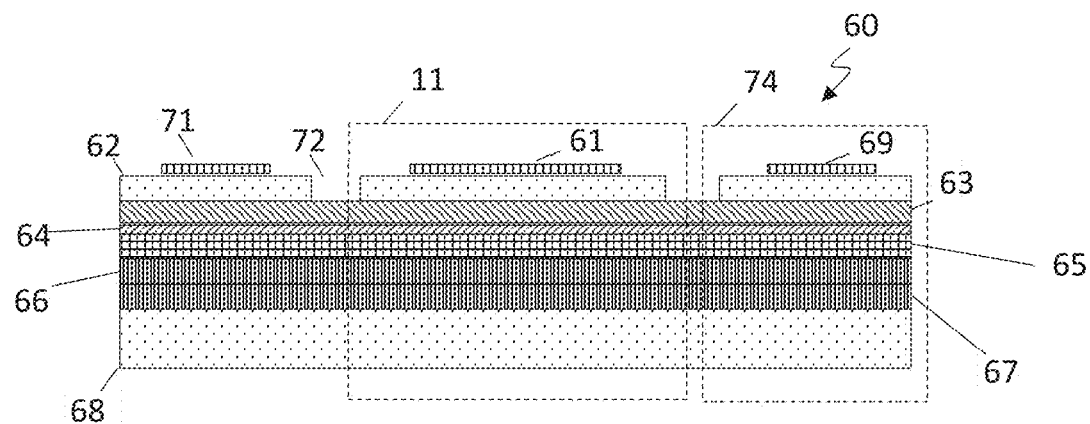
FIG. 3a illustrates a cross section of a device according to the present disclosure.

FIG. 3a illustrates a cross section of a photonic integrated circuit according to the present disclosure. Next to the ERM 11 there will be an isolation section 72 on both sides, and next to the isolation sections 72 there will be another short ERM section that is to be connected to ground 71. A waveguide 74 comprises a waveguiding layer 65, and is arranged for conducting light waves. The waveguide 74 also comprises conducting contacts 69 that allow either a connection to a voltage source or to an electrical ground according to the present disclosure.

The length of the isolation section then determines the dark current of the ERM to a large extent. A typical length of an isolation section 72 is currently 50 µm. This length stems from the current design rules of the Smart Photonics process. However this length can be in principle be shortened to approximately 20 µm if the etch depth (down to approx. halfway layer III-1) of the section is similar and if the application allows for the increase dark current on the ERM. The limit of 20 µm stems from the fabrication process of the currently used metallization process (a lift-off process).

The length of the grounding section will be also be 50 µm determined by the current design rule. It could be shorter. The currents that will flow are estimated to be at most in the order of a microampere. Therefore even a 20 µm long grounding contact (a practical limit in the current technology) is not expected to have a prohibitively large electrically resistance. For the etch depth it is important that the highly doped layer III-2 is fully etched away. Less deep etching in the waveguide for isolation is possible, but current levels from the ERM to the grounding contact will start to rise. It depends on the application of the circuit and electronics if this is tolerable. The metallization used for the ground contacts can be the same as that for the phase modulators. For example, the contacts are made from any of Titanium/Platinum/Gold, Ti/Pt/Au, contact with 300 Nano metre, nm, thickness for the gold deposited by evaporation.

It should be noted that photonic integrated devices on InP are described here, but in principle other integration schemes that use similar ridge waveguide technology and other semiconductor systems would have similar issues. However we are not aware of other material systems being used commercially to this purpose.

Figure 3B:
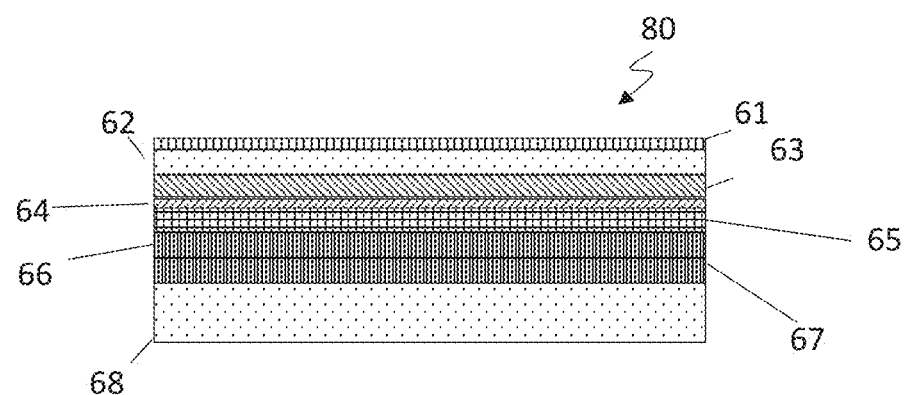
FIG. 3b illustrates the different layers of a device according to the present disclosure.

The additional ground contacts 71 as in FIG. 3 are all contacted using metal routing on the chip surface in the current Smart Photonics integration scheme. This will lead to a large number of metal connections on the chip. The different layers are further elaborated with the help of FIG. 3b.

FIG. 3b illustrates the different layers of a device according to the present disclosure. FIG. 3b and the corresponding description is to be understood as an example. The features of the present disclosure are not limited to the exact values as presented here. Layer III-3, indicated as 61, is a p-doped contact layer with a high doping concentration of the order of 1.5E19. A typical material employed may be a p-doped InGaAs. Layer 61 is 300 nm thick. Layer III-2, indicated as 62, is also p-doped, but has a lower doping concentration of the order of 1E18 per cubic centimetre, $cm^{-3}$. Layer 62 is made of InP and has a thickness of 1000 nm.

Layer III-1, indicated as 63, is a p-doped layer made of InP, that is about 300 nm thick. This layer has a lower doping concentration of the order of 1E17 $cm^{-3}$. Layer II-2, indicated as 64, is an n-doped layer made of InP, that is about 200 nm thick. The doping concentration is of the order of 1E16 $cm^{-3}$. Layer II-1, indicated as 65, is an n-Q1.25 waveguide layer. The waveguide layer 65 has a doping concentration of about 1E16 $cm^{-3}$ and is 500 nm thick.

Layers I-2 and I-1, indicated as 66 and 67 respectively, are both n-doped and have a doping concentration of 1E17 $cm^{-3}$ and 1E18 $cm^{-3}$ respectively. They are both made of InP and have thickness of 500 nm each. Layer 68 is the substrate on which all the subsequent layers have been assembled. It is also referred to as I-0 and is usually an n-doped InP with a doping concentration of 1E18 $cm^{-3}$ to 4E18 $cm^{-3}$. As mentioned previously, the values are merely exemplary and are not limiting.

Figure 3C:
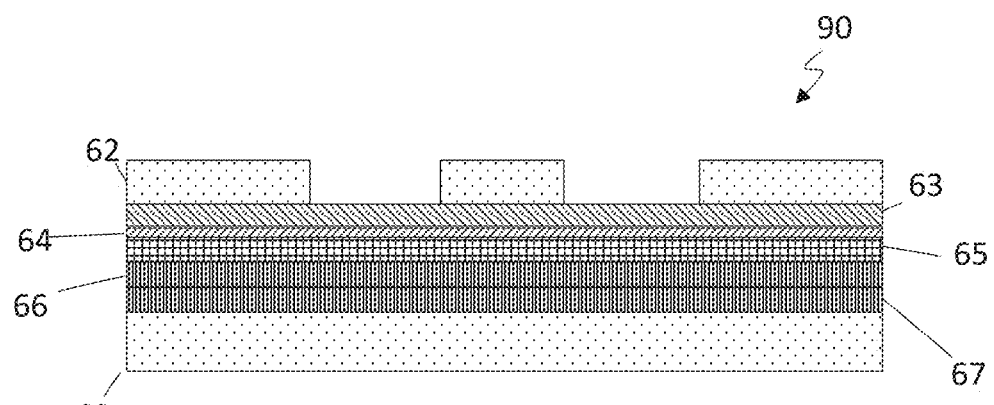
FIG. 3c illustrates a cross section of a device according to the present disclosure.

FIG. 3c illustrates a cross section of a device according to the present disclosure. There are a number of issues to be considered. It is possible that the isolation in the perpendicular direction of the waveguides needs to be considered. The trenches next to the passive waveguides are 20 µm wide as shown in FIG. 3c. The etching is deeper than the isolation etch, but the distance is typically three to five times, maybe more, smaller.

Figure 4:
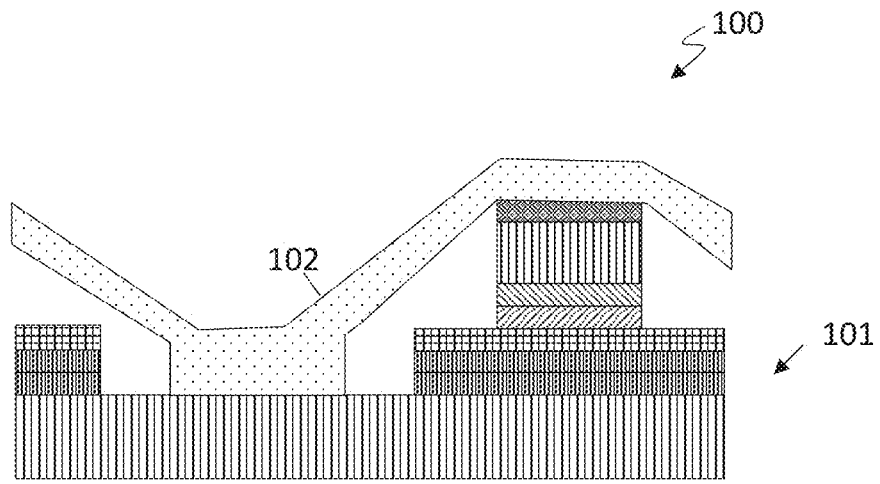
FIG. 4 illustrates a cross section of a grounded waveguide section according to the present disclosure.

FIG. 4 illustrates, in 100, a cross section of a grounded waveguide section according to the present disclosure. The invention is more general that providing contacts on phase modulators. It also applies to other reverse biased components such as amplifiers used in detectors, as well as in passive components. Another point is that it may be wise to contact all passive components and keep them at a reverse bias voltage of approximately 3 to 4 Volts. There are a number of reasons one might want to do this. Having contacts 102 on all passive devices solves the issue of the electrical isolation using far fewer required contacts (without changing the technology). The design of contacts for passive components may be slightly different than FIG. 4.

The cross-section of the waveguide would be similar to that in FIG. 4. In case one would want to contact passive devices such as a multi-mode interference coupler, the waveguide section will become significantly wider (e.g. 8 µm instead of 2 µm). Metallization of such wider structures may pose issues in the fabrication. The application of the voltage also reduces the free carrier concentration in the waveguides and thus reduces the propagation loss by up to 0.5 dB per cm. It also clears out the free carriers that are produced in the passive waveguide by the light going through the waveguide which can induce increased absorption. The maximum power handling of a passive waveguide may possibly be increased as well but this needs to be investigated. A third advantage is that the carriers induced by the light create phase noise on the optical signal. This can be an issue in very narrow linewidth CW lasers and definitely plays a role in mode-locked lasers. The free carrier concentration will vary with time due to thermal effects but also the built-in potential of the PIN structure makes that the waveguides forward biases itself (like a solar cell) in a way that is hard to predict. This light generated current can go anywhere in the p-doped layers and flow to waveguide sections with lower intensity. The free carrier effects in the passive waveguides are currently under investigation.

Figure 5:
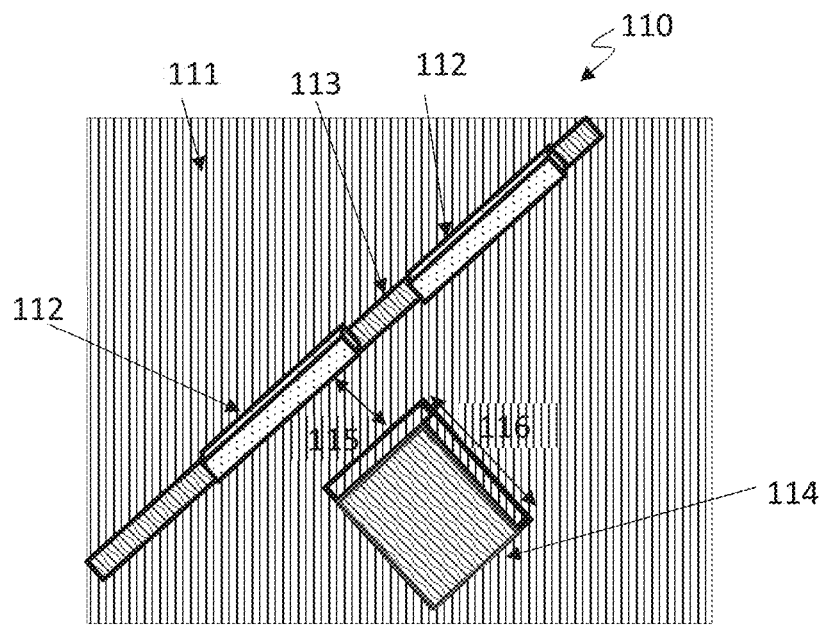
FIG. 5 illustrates a three dimensional sketch of a waveguide ridge with two isolation section, a grounding section and an opening to a substrate layer.

FIG. 5 illustrates a three dimensional sketch 110 of a waveguide ridge with two isolation section 112, a grounding section 113 and an opening 114 to a substrate layer 111. One possible way to avoid this is to make a local contact to the n-doped layers in the substrate as depicted schematically in FIG. 4. This will require a change in the existing processing scheme. A hole will have to be etched next to the waveguide where the contact to the waveguide to the highly doped layer I-0.

A metallization scheme such as the currently used Ti—Pt—Au layer system (typical 60-75-500 nm thickness respectively) and contact annealing can be used since it will provide a good Ohmic contact on both n doped InP and p doped InGaAs. The size 116 of the opening 114 towards the layer I-0 can be equally long as the grounding contact and it is estimated it will need to be minimally 20 µm wide. In FIG. 5 a drawing to scale is presented of a 2 µm wide ridge waveguide, with two 20 µm isolation sections, a 20 µm long grounding section in the middle and the opening for access to layer I-0, before planarization and metallization are applied to show the structure. The opening 114 is 10 µm away, 115, from the waveguide in order not to affect the light propagation in the waveguide.

Since current levels are expected to be limited to 1 µA or less, the resistance value of the contact may be relatively high (e.g. several hundred Ω). It might be that the etched hole may be of the same depth as that of the deeply etched ridge waveguides in which case the metal would be contacted a lower doped InP layer. This needs more investigation and trials.

The grounding of the p-side of the waveguide will be more easily achieved in the semi-insulating substrate technology. In this technology scheme where a top n-contact level is already available that can be used to connect the top p-contacts of the grounded waveguide section.

These combinations of two isolation sections and one grounding section can also be used together with other reverse biased components. A specific example is a photo-detector where it will prevent leakage current and therefore a dark current level, to other detectors or biased components as well as dark currents due to photo-generated currents in other passive waveguide components connected to the photodetector.

The electrical isolation of the phase modulator building block in the Smart Photonics platform needs to be addressed. A possible solution is to add grounding contacts adjacent to the phase modulator separated by isolation sections. The grounding contacts can in principle be realized by making a contact locally to the n-side of the chip. There are arguments to have all passive components contacted and kept at ground voltage connected to the n-side, or at a reverse bias voltage of a few volts to reduce propagation losses and possibly stabilize the optical path length to a higher degree than the current situation.

Generally, the invention includes the use of ground contacts and isolation sections to prevent cross-talk between any elements in Smart Photonics platform, both active and passive. The application to electro-optic phase modulators is just one example of an active component.

What is claimed is:

1. A photonic integrated circuit, PIC, comprising a plurality of semiconductor layers on a substrate, the plurality of semiconductor layers forming at least one of a PIN or PN doping structure, the PIC comprising:
    a waveguide arranged for conducting light waves, the waveguide comprising at least part of a waveguiding layer, which is one of the layers of the plurality of semiconductor layers;
    an optical element comprising at least part of the waveguiding layer, which is one of the layers of the plurality of semiconductor layers, wherein the at least parts of the waveguiding layer of the waveguide and the optical element are connected to one another, wherein the optical element is operable in reverse-bias mode, and wherein the optical element comprises a contact layer arranged for connecting to a voltage source;
    a plurality of conducting contacts connected to one another by a metallic conducting layer, wherein the waveguide comprises at least one conducting contact of the plurality of conducting contacts, the at least one conducting contact proximal to the optical element; and
    at least one isolation section arranged between the contact layer and the at least one conducting contact.

2. The photonic integrated circuit according to claim 1, wherein the at least one isolation section is arranged between the optical element and the at least one conducting contact.

3. The photonic integrated circuit according to claim 2, wherein the at least one conducting contact is configured on both sides of the optical element with respect to a direction of the light waves in the waveguide.

4. The photonic integrated circuit according to claim 1, wherein the at least one conducting contact is configured on both sides of the optical element with respect to a direction of the light waves in the waveguide.

5. The photonic integrated circuit according to claim 1, wherein the at least one conducting contact extends over substantially the entire waveguide.

6. The photonic integrated circuit according to claim 1, wherein at least one of:
    the at least one isolation section is arranged between the optical element and the at least one conducting contact, and the at least one conducting contact extends over substantially the entire waveguide; or
    the at least one conducting contact is configured on both sides of the optical element with respect to a direction of the light waves in the waveguide, and the at least one conducting contact extends over substantially the entire waveguide.

7. The photonic integrated circuit according to claim 1, wherein the at least one conducting contact is connected to an electrical ground.

8. The photonic integrated circuit according to claim 7, wherein the PIC further comprises a grounding hole arranged for allowing a contact between the at least one conducting contact and an n-doped layer wherein distance between an edge of the grounding hole and the waveguide is at least 10 µm, the distance being measured in a direction perpendicular to that of propagation of light in the waveguiding layer.

9. The photonic integrated circuit according to claim 8, wherein at least one dimension of a cross section of the grounding hole in a plane parallel to the direction of propagation of light in the waveguiding layer is at least 20 µm.

10. The photonic integrated circuit according to claim 1, wherein the length of the at least one conducting contact measured in a direction of propagation of light in the waveguiding layer is at least 20 µm.

11. The photonic integrated circuit in accordance with claim 1, wherein the at least one conducting contact comprises at least one of Titanium, Gold or Platinum.

12. The photonic integrated circuit according to claim 1 wherein the optical element is at least one of a
Electro-Refractive Modulator, ERM, or
Photodetector.

13. A photonic integrated circuit, PIC, comprising a plurality of semiconductor layers on a substrate, the plurality of semiconductor layers forming at least one of a PIN or PN doping structure, the PIC comprising:
a waveguide arranged for conducting light waves, the waveguide comprising a waveguiding layer, which is one of the layers of the plurality of semiconductor layers;
an optical element comprising a waveguiding layer, which is one of the layers of the plurality of semiconductor layers, which waveguiding layers of the waveguide and the optical element are connected to one another, wherein the optical element is operable in reverse-bias mode, and wherein the optical element comprises a contact layer arranged for connecting to a voltage source, wherein the waveguide comprises at least one conducting contact proximal to the optical element, and wherein at least one of:
the at least one conducting contact is connected to an electrical ground,
the optical element is an electro refractive modulator, or
the optical element is a photodetector; and
at least one isolation section arranged between the contact layer and the at least one conducting contact.

14. A method of fabricating a photonic integrated circuit, PIC, comprising providing a plurality of semiconductor layers on a substrate, the plurality of semiconductor layers forming at least one of a PIN or PN doping structure, the PIC comprising:
a waveguide arranged for conducting light waves, the waveguide comprising a waveguiding layer, which is one of the layers of the plurality of semiconductor layers;
an optical element comprising a waveguiding layer, which is one of the layers of the plurality of semiconductor layers, which waveguiding layers of the waveguide and the optical element are connected to one another, wherein the optical element is operable in reverse-bias mode, and wherein the optical element comprises a contact layer arranged for connecting to a voltage source, wherein the waveguide comprises at least one conducting contact proximal to the optical element, and wherein at least one of:
the at least one conducting contact is connected to an electrical ground,
the optical element is an electro refractive modulator, or
the optical element is a photodetector; and
at least one isolation section arranged between the contact layer and the at least one conducting contact.

15. A method of fabricating a photonic integrated circuit, PIC, comprising providing a plurality of semiconductor layers on a substrate, the plurality of semiconductor layers forming at least one of a PIN or PN doping structure, the PIC comprising:
a waveguide arranged for conducting light waves, the waveguide comprising at least part of a waveguiding layer, which is one of the layers of the plurality of semiconductor layers;
an optical element comprising at least part of the waveguiding layer, which is one of the layers of the plurality of semiconductor layers, wherein the at least parts of the waveguiding layer of the waveguide and the optical element are connected to one another, wherein the optical element is operable in reverse-bias mode, and wherein the optical element comprises a contact layer arranged for connecting to a voltage source;
a plurality of conducting contacts connected to one another by a metallic conducting layer, wherein the waveguide comprises at least one conducting contact of the plurality of conducting contacts, the at least one conducting contact proximal to the optical element; and
at least one isolation section arranged between the contact layer and the at least one conducting contact.

16. The method of fabricating a photonic integrated circuit according to claim 15, wherein the optical element is any at least one of a
Electro-Refractive Modulator, ERM, or
Photodetector.

17. The method of fabricating a photonic integrated circuit according to claim 15, wherein the at least one isolation section is arranged between the optical element and the at least one conducting contact.

18. The method of fabricating a photonic integrated circuit according to claim 15, wherein the at least one conducting contact is configured on both sides of the optical element with respect to a direction of the light waves in the waveguide.

19. The method of fabricating a photonic integrated circuit according to claim 15, wherein the at least one conducting contact extends over substantially the entire waveguide.

* * * * *